US00PP22975P3

(12) United States Plant Patent
Grard et al.

(10) Patent No.: US PP22,975 P3
(45) Date of Patent: Aug. 21, 2012

(54) APPLE TREE NAMED 'GRADIROSE'

(50) Latin Name: ***Malus domestica* (Borkh.)**
Varietal Denomination: Gradirose

(76) Inventors: Alexandre Grard, Mudaison (FR); Olivier Grard, Mudaison (FR)

( * ) Notice: Subject to any disclaimer, the term of this patent is extended or adjusted under 35 U.S.C. 154(b) by 0 days.

(21) Appl. No.: 12/807,458

(22) Filed: Sep. 3, 2010

(65) Prior Publication Data

US 2011/0126331 P1 May 26, 2011

Related U.S. Application Data

(60) Provisional application No. 61/276,490, filed on Sep. 11, 2009.

(51) Int. Cl.
*A01H 5/00* (2006.01)

(52) U.S. Cl. ..... Plt./161

(58) Field of Classification Search ..... Plt./161
See application file for complete search history.

(56) References Cited

OTHER PUBLICATIONS

GTITM UPOVROM Citation for 'Gradirose' as per QZ PBR20042210; Nov. 15, 2004.*
GTITM UPOVROM Citation for 'Grandirose' as per CH PBR08-2489; May 9, 2008.*
GTITM UPOVROM Citation for 'Grandirose' as per FR NLI1016474; Feb. 20, 2006.*

* cited by examiner

*Primary Examiner* — Kent L Bell
(74) *Attorney, Agent, or Firm* — Ballew Law

(57) ABSTRACT

'Gradirose' is a new and distinct apple tree notable for its semi-upright plant habit, skin over color, early timing of fruit ripening, and fruit quality.

5 Drawing Sheets

Latin name of the genus and species of the plant claimed: *Malus domestica* (Borkh.).
Variety denomination: 'Gradirose'.

STATEMENT REGARDING FEDERALLY SPONSORED RESEARCH OR DEVELOPMENT

None.

BACKGROUND OF THE INVENTION

The present invention relates to a new and distinct cultivar of apple tree, botanically known as *Malus domestica*, and hereinafter referred to by the name 'Gradirose'.

The new apple variety 'Gradirose' originated from an open-pollination in Hérault, France of *Malus domestica* 'Christmas Rose', (not patented), as the female, or seed parent, with an unknown selection of *Malus domestica*, as the male or pollen, parent. The new Apple tree was discovered and selected by the inventors as a single plant from within the progeny of the stated open-pollination in a controlled environment in Hérault, France in 1991.

Asexual propagation by grafting was first carried out in Maguio, France. Gradirose has been asexually reproduced by budding and grafting, since 1994 in Hérault, France, and has demonstrated that the new variety reproduces true to type with all of the characteristics, as herein described, firmly fixed and retained through successive generations.

SUMMARY OF THE INVENTION

The following characteristics of the new variety have been repeatedly observed and can be used to distinguish 'Gradirose' as a new and distinct cultivar of apple:

1. Semi-upright plant habit.
2. Skin over color.
3. Early timing of fruit ripening.
4. Fruit quality.

'Gradirose' can be compared to both 'Cripps Pink' and Golden Delicious (not patented). Fruit of the new variety is mature and ready for harvest about 60 days earlier than the fruit of 'Cripps Pink'. 'Gradirose' is similar to Golden Delicious as a heavy producer, but the fruit skin color of 'Gradirose' is pink red in color whereas the fruit skin color of 'Golden Delicious' is yellowish green in color.

BRIEF DESCRIPTION OF THE PHOTOGRAPHS

Figure 1:
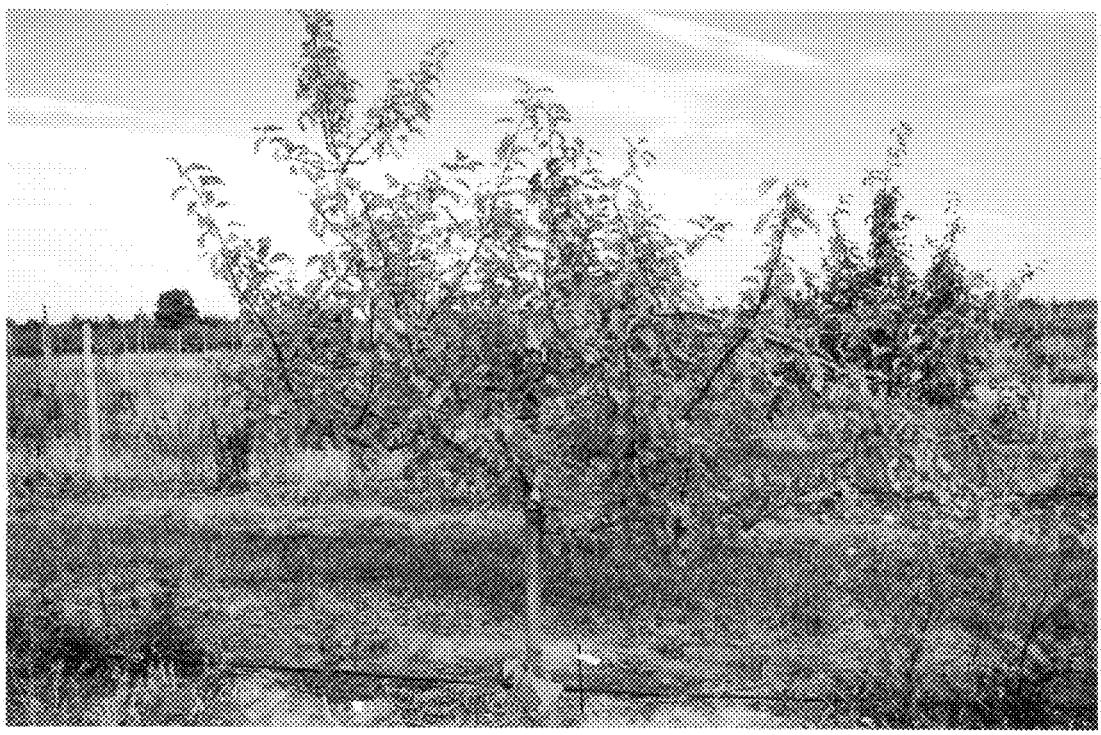
Figure 2:
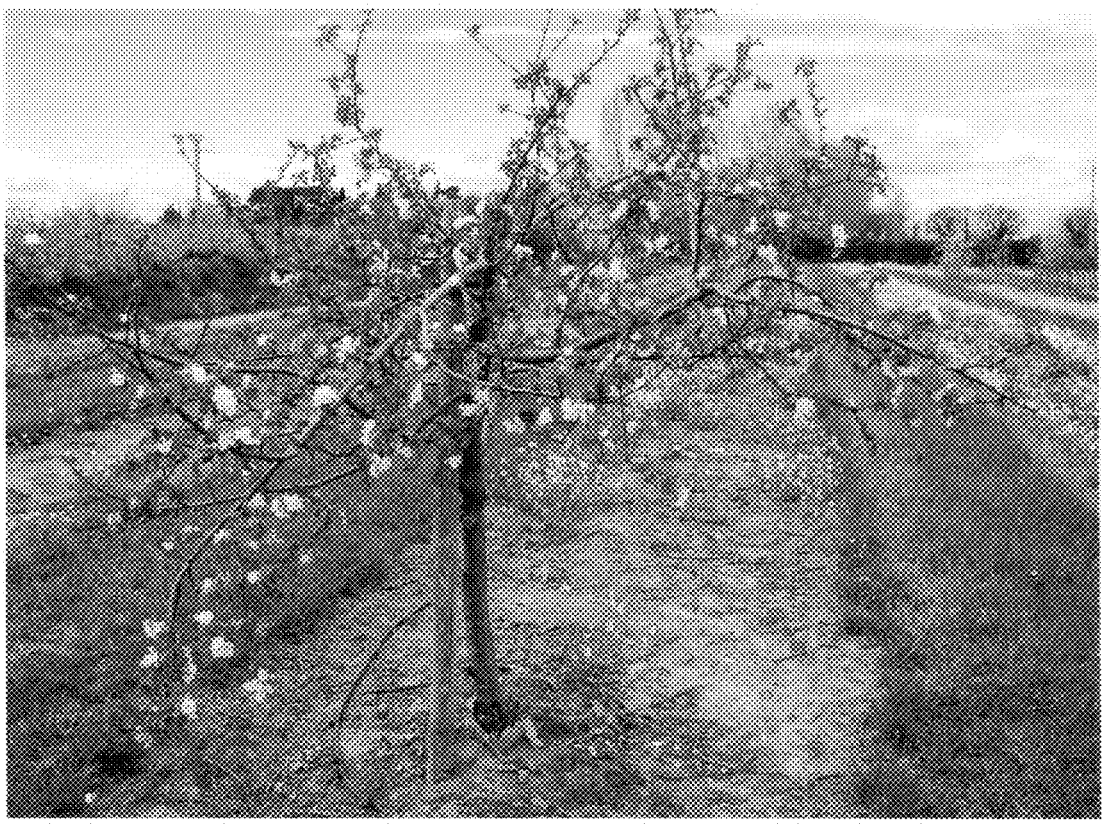
Figure 3:
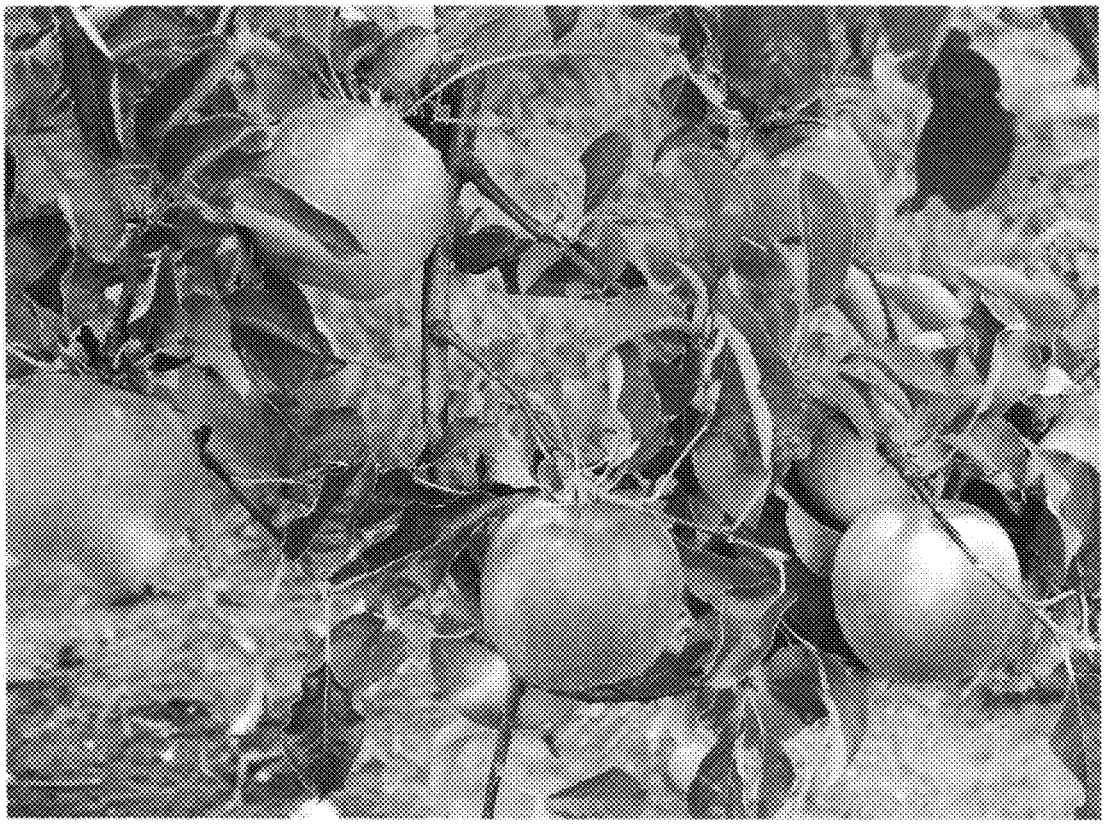
Figure 4:
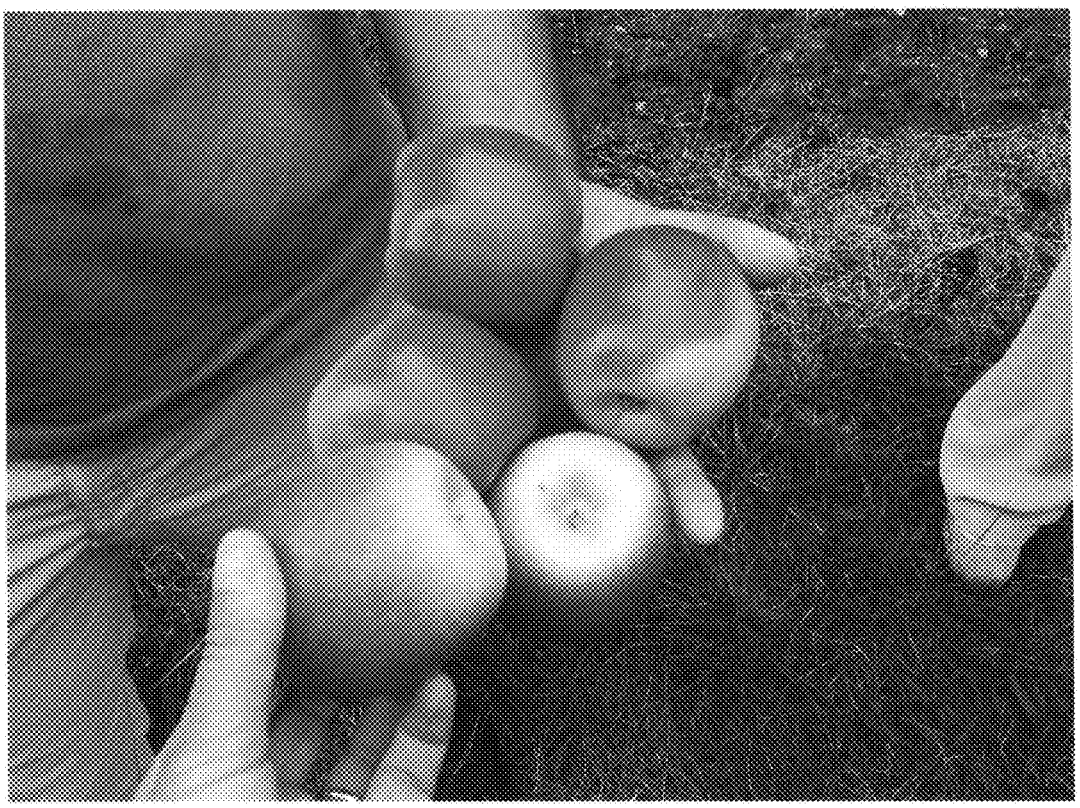
Figure 5:
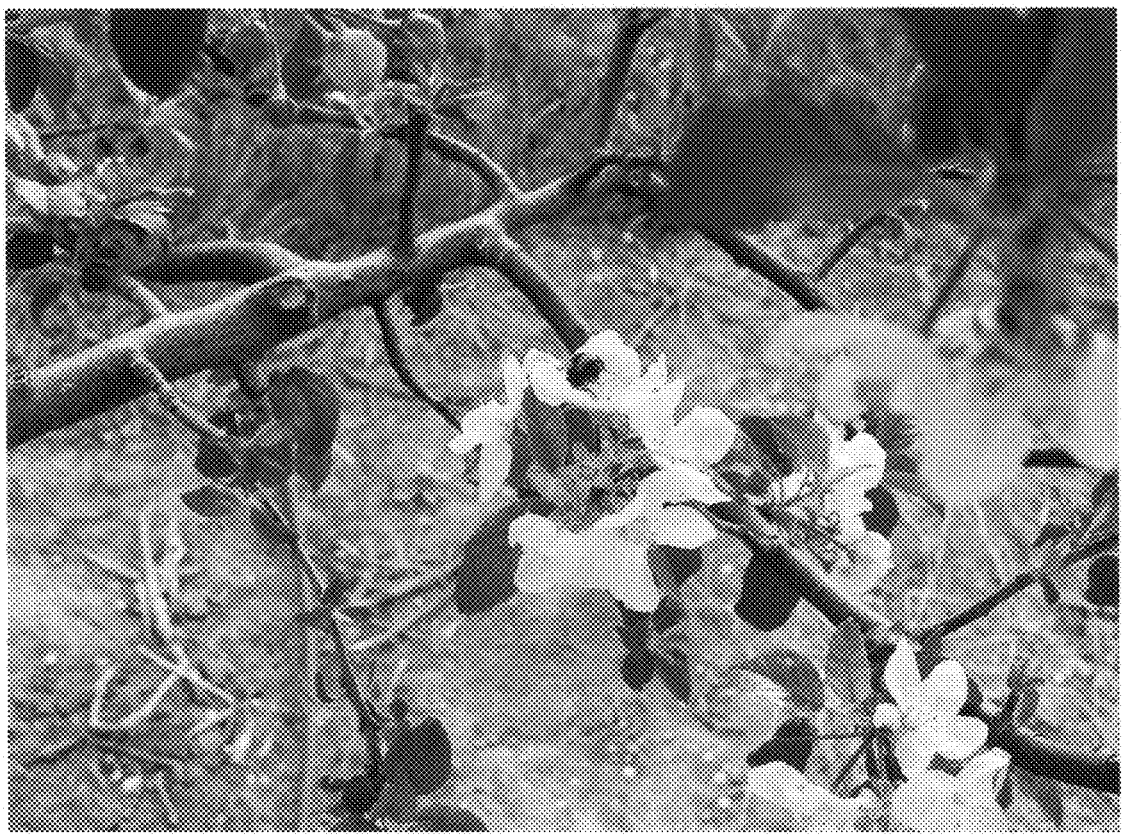

FIG. 1 shows the tree of the new variety;
FIG. 2 shows the tree and flower of the new variety;
FIG. 3 shows the fruit and leaves of the new variety;
FIG. 4 shows the fruit of the new variety; and
FIG. 5 shows the blossom of the new variety.

DETAILED BOTANICAL DESCRIPTION

The following detailed botanical description is based on observations of trees planted in 1995, and described during the 2003 and 2004 growing seasons at Hérault, France. Color descriptions refer to The Royal Horticultural Society Colour Chart (1995). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Botanical classification: *Malus domestica* Borkh cultivar Gradirose.

Parentage:

*Female, or seed parent.*—*Malus domestica* 'Christmas Rose', not patented.

*Male, or pollen, parent.*—Unknown selection of *Malus domestica*, not patented.

Tree:

*Vigor.*—Vigorous.

*Habit.*—Semi-Upright.

*Size.*—Height: 3.0 m.

*Bearing.*—Annual bearing habit on spurs and long shoots.

*Trunk.*—Diameter: 15-20 cm at 30 cm above graft union; bark texture smooth; color brown RHS N200C; Lenticels: Absent.

*Winter hardiness.*—Average in area tested.

*Branches.*—1 m above graft union; length 150 cm; diameter 7.0 cm; crotch angle 70°; color light brown RHS N200D. Approximately 20 branches per tree; Texture: thick, hard and smooth; Internode length medium to long; Lenticels: Medium to high density 7-9 per $cm^2$; color yellow white RHS 158D.

Dormant one year old shoot:

*Size.*—Diameter 4-5 mm; Length 20-30 cm.

*Color.*—Brown RHS 200C.

*Internode length.*—2.0 cm.

*Pubescence.*—Very strong.

*Lenticels.*—Length 0.9-1.0 mm, width 0.8-1.0 mm; density 1-2/$cm^2$.

Flowers:

*Bud.*—Quantity per spur 4 to 5; shape globose; color red-purple RHS 63A; Diameter 10-12 mm.

*Petals.*—Quantity per flower 5; Aspect free to overlapping; Texture smooth, surface is wavy; Shape ovate; Length 16-18 mm; Width 15-16 mm; upper surface color white RHS155D; Lower surface color white RHS 155D with traces of pink RHS 68B in veins and edges when fully open.

*Flower.*—Diameter of fully open flower 2 cm; Depth 0.7 cm; Quantity per cluster 4.

*Sepals.*—Quantity per flower 5; Shape triangular; color green RHS 135B.

*Pedicel.*—Length 19-21 mm; Diameter 2 mm; Color greyed-purple RHS 187A.

*Pistil.*—Length 13-14 mm; Color yellow-green RHS 145C.

*Anthers.*—Quantity per flower 16; length 2 mm; pollen color yellow RHS 12B.

*Stigma.*—Width 1 mm; Color RHS 11C.

*Style.*—Length 7 mm; color yellow-green RHS 145C.

*Bloom period.*—Early to Mid Season; first bloom April 8, full bloom April 12 at Hérault, France.

*Fragrance.*—Faint.

Leaf:

*Attitude in relation to shoot.*—Outwards.

*Size.*—Length 10-11 cm; Width 5.0-6.0 cm; Length to Width Ratio 1.8-2.0.

*Margin.*—Serrate.

*Texture.*—Smooth.

*Pubescence.*—Upper surface weak to absent; Lower surface medium to strong.

*Color.*—Upper surface green RHS 137A; lower surface green RHS 138B.

*Shape.*—Ovate; apex acuminate; base aequilateral.

*Veins.*—Venation Type: Net-like; Medium dense; Upper surface yellow-green RHS 145B; Lower surface yellow-green RHS 145C.

*Petiole.*—Length 1.5-2.0 cm; width 2 mm; color yellow-green RHS 144C.

Fruit:

*Size.*—Weight 150 g; diameter 75-90 mm.

*Height.*—9-10 cm.

*Fruit shape.*—Ellipsoid.

*Stalk lenticels.*—Absent.

*Position of maximum diameter.*—Top.

*Ribbing.*—Absent.

*Aperture of eye.*—Closed.

*Depth of eye basin.*—8-10 mm.

*Width of eye basin.*—35-40 mm.

*Stalk.*—Diameter 3 mm; length 18-22 mm; Color RHS 199B.

*Depth of stalk cavity.*—11-13 mm.

*Width of stalk cavity.*—20 mm.

*Lenticels.*—Size 0.6-0.8 mm; density 9-11/$cm^2$.

*Bloom of skin.*—Absent.

*Greasiness of skin.*—Absent.

*Ground color of skin.*—Yellow-green RHS 154B.

*Over color of skin.*—Pink-Red RHS 47C.

*Skin thickness.*—Thick.

*Skin texture.*—Smooth.

*Skin firmness.*—Soft.

*Amount of over color.*—50-80 percent.

*Pattern of over color.*—Solid flush with weakly defined stripes.

*Brix.*—13-15°.

*Flesh.*—Texture juicy, firm, about 9.5 kg/$cm^2$; Aroma strong; medium eating quality; color white RHS 155C.

*Seeds.*—Quantity per fruit 6-8; seeds per locule 2; teardrop shape; color brown RHS 200B.

*Core.*—Few, Symmetrical, Length 30 mm-32 mm, Width 29 mm-30 mm.

*Locules.*—Quantity per fruit 5; length 1 cm; width 0.3-0.5 cm.

*Harvest date.*—First Harvest Date — Aug. 27, 2010 and last Harvest Date — Sep. 5, 2010 in southern France.

*Production.*—60 to 80 tons of fruit produced per hectare.

*Keeping quality.*—Good, 4-5 months.

*Use.*—Fresh market.

*Resistance/susceptibility to known diseases/pests.*—Susceptible to grey aphids.

We claim:

1. A new and distinct apple tree substantially as shown and described herein.

* * * * *